United States Patent
Hansenne et al.

(12)

(10) Patent No.: US 6,569,409 B1
(45) Date of Patent: May 27, 2003

(54) METHOD FOR PROVIDING DIBENZOYLMETHANE DERIVATIVES WITH LIGHT STABILITY

(75) Inventors: Isabelle Hansenne, Westfield, NJ (US); Martin Josso, Paris (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/743,224

(22) PCT Filed: Jun. 9, 1999

(86) PCT No.: PCT/FR99/01366

§ 371 (c)(1),
(2), (4) Date: Mar. 28, 2001

(87) PCT Pub. No.: WO00/02528

PCT Pub. Date: Jan. 20, 2000

(30) Foreign Application Priority Data

Jul. 8, 1999 (FR) ............................................ 98/08765

(51) Int. Cl.$^7$ .................................................. A61K 7/42

(52) U.S. Cl. ......................................... 424/59; 424/401

(58) Field of Search ..................................... 424/401.59

(56) References Cited

U.S. PATENT DOCUMENTS 5,736,125 A  *  4/1998  Morawsky et al. ........... 424/59

FOREIGN PATENT DOCUMENTS

| EP | 0 685 227 | 12/1995 |
| FR | 2 398 496 | 2/1979 |

* cited by examiner

Primary Examiner—Jose G. Dees
Assistant Examiner—Konata M. George
(74) Attorney, Agent, or Firm—Burns, Doane, Swecker & Mathis, L.L.P.

(57) ABSTRACT

The invention concerns novel light-stable filtering cosmetic compositions for topically protecting the skin and/or the hair against ultraviolet radiation, in particular solar radiation, comprising in a cosmetically acceptable support, at least a dibenzoylmethane derivative and at least an oily phase, and an efficient amount of at least a thickening copolymer including at least a hydrophobic unit in sufficient amount for it to be partially or completely soluble in the oily phase and at least a hydrophilic unit in sufficient amount for thickening the oily phase as stabilizing agent for the filter. The invention also concerns the corresponding method for providing dibenzoylmethane with light stability and the use of the compositions for skin and hair protection against the effects of ultraviolet radiation.

34 Claims, No Drawings

METHOD FOR PROVIDING DIBENZOYLMETHANE DERIVATIVES WITH LIGHT STABILITY

The present invention relates, among other subject matters, to novel cosmetic compositions for topical use specifically intended for the photoprotection of the skin and/or hair against ultraviolet radiation (compositions hereinbelow known more simply as antisun compositions or screening compositions), to their use in the abovementioned cosmetic application and to a general process for the photostabilization of specific sunscreen agents, active in the UV-A region, by means of one or more suitably selected compounds.

More specifically still, it relates to antisun compositions which are photostable with regard to UV radiation and which comprise, in a cosmetically acceptable vehicle, at least one oily phase and at least one compound of the type derived from dibenzoylmethane, in combination with at least one specific thickening copolymer, as photostabilizing agent. It also relates to the corresponding process for the stabilization of said UV-A screening agent or agents by means of said thickening polymer or polymers.

It is known that UV-A rays with wavelengths of between 320 and 400 nm cause tanning of the skin but that they are also capable of inducing, in the long term, a detrimental change in the latter, in particular in the case of sensitive skin or of skin continually exposed to solar radiation. UV-A rays cause in particular a loss of elasticity of the skin and the appearance of wrinkles, leading to premature ageing. In addition, they promote triggering of the erythematous reaction or accentuate this reaction in some subjects and can even be the cause of phototoxic or photo-allergic reactions. It is thus desirable to screen out UV-A radiation.

Numerous organic sunscreen agents capable of absorbing harmful UV-A rays more or less selectively have been provided to date in the field of cosmetics.

In this respect, a particularly advantageous family of UV-A screening agents is currently composed of dibenzoylmethane derivatives and in particular 4-(tert-butyl)-4'-methoxydibenzoylmethane; this is because these derivatives exhibit a high intrinsic absorption power. These dibenzoylmethane derivatives are now products which are well known per se as lipophilic screening agents active in the UV-A region and are disclosed in particular in French patent applications FR-A-2 326 405 and FR-A-2 440 933 and in European patent application EP-A-0 114 607; furthermore, 4-(tert-butyl)-4'-methoxydibenzoylmethane is currently offered for sale under the trade name of "Parsol 1789" by Givaudan.

Unfortunately, it is found that dibenzoylmethane derivatives are products which are relatively sensitive to ultraviolet radiation (in particular UV-A radiation), that is to say, more specifically, that they have an unfortunate tendency to decompose more or less rapidly under the effect of the latter. Thus, this substantial lack of photochemical stability of dibenzoylmethane derivatives in the face of ultraviolet radiation, to which they are naturally intended to be subjected, does not make it possible to guarantee constant protection during prolonged exposure to the sun, so that repeated applications at regular and frequent intervals have to be carried out by the user in order to obtain effective protection of the skin against UV rays.

The photostabilization of dibenzoylmethane derivatives with respect to UV radiation constitutes, to date, a problem which has not yet been solved in a completely satisfactory manner.

In point of fact, the Applicant Company has now just discovered, unexpectedly and surprisingly, that, by combining the abovementioned dibenzoylmethane derivatives, in a vehicle comprising at least one oily phase, with an effective amount of at least one specific thickening polymer which will be defined in more detail below, it is possible to improve, substantially and notably, the photochemical stability (or photostability) of these same dibenzoylmethane derivatives without affecting the stability over time of their photoprotective effectiveness in the UV-A region.

This essential discovery forms the basis of the present invention.

Thus, in accordance with one of the subject matters of the present invention, a novel process for the stabilization of dibenzoylmethane derivatives with respect to UV radiation (wavelengths of between 280 nm and 400 nm approximately), in particular solar radiation, when these screening agents are present in a vehicle comprising at least one oily phase, is now provided, said process being essentially characterized in that it consists in combining said dibenzoylmethane derivatives with an effective amount of at least one specific thickening polymer which will be defined in more detail below.

In accordance with another subject matter of the present invention, novel photostable screening cosmetic compositions intended for the protection of the skin and/or hair against ultraviolet radiation, in particular solar radiation, are also provided, of the type comprising, in a cosmetically acceptable vehicle, at least one dibenzoylmethane derivative and at least one oily phase, which compositions are essentially characterized in that they additionally comprise an effective amount of at least one specific thickening copolymer which will be defined in more detail below.

The expression "effective amount of thickening copolymer in accordance with the invention" is understood to mean an amount sufficient to produce a notable and significant improvement in the photostability of the dibenzoylmethane derivative or derivatives of the photoprotective cosmetic composition. This minimum amount of stabilizing agent to be employed, which can vary according to the nature of the cosmetically acceptable vehicle used for the composition, can be determined without any difficulty by means of a conventional test for the measurement of photostability, such as that given in the examples below.

Yet another subject matter of the present invention is an improved cosmetic treatment process for the protection of the skin and/or hair against ultra-violet radiation, in particular solar radiation, which consists essentially in applying, to the latter, an effective amount of a photostable composition in accordance with the invention.

Finally, another subject matter of the present invention is the use of the same specific thickening polymers for stabilizing, with respect to UV rays, a dibenzoylmethane derivative present in a cosmetic composition comprising at least one oily phase.

Other characteristics, aspects and advantages of the present invention will become apparent on reading the detailed description which will follow.

As indicated above, the dibenzoylmethane derivatives intended to be photostabilized in the context of the present invention are products which are already well known per se and which are disclosed in particular in the abovementioned documents FR-A-2 326 405, FR-A-2 440 933 and EP-A-0 114 607, the teachings of which documents are, as regards that which affects the actual definition of these products, entirely included by way of references in the present description.

According to the present invention, one or more dibenzoylmethane derivatives can, of course, be employed.

Mention may in particular be made, among the dibenzoylmethane derivatives coming particularly well within the scope of the present invention, without implied limitation, of:

2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane
4-tert-butyl-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane Preference is very particularly given according to the present invention, among the abovementioned dibenzoylmethane derivatives, to the use of 4-(tert-butyl)-4'-methoxydibenzoylmethane, in particular that offered for sale under the trade name of "Parsol 1789" by Givaudan, this screening agent thus corresponding to the following expanded formula:

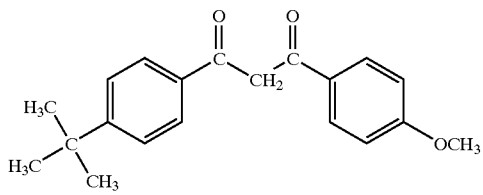

Another dibenzoylmethane derivative which is preferred according to the present invention is 4-isopropyldibenzoylmethane, a screening agent sold under the name of "Eusolex 8020" by Merck which corresponds to the following expanded formula:

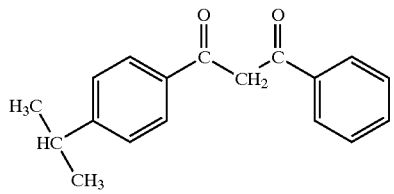

The dibenzoylmethane derivative or derivatives can be present in the compositions in accordance with the invention or in the compositions intended to be stabilized in accordance with the process of the invention at contents which are generally between 0.01% and 10% by weight and preferably at contents of between 0.1% and 6% by weight with respect to the total weight of the composition.

The thickening polymers in accordance with the present invention are copolymers comprising at least one hydrophobic unit, in an amount sufficient to result in its partial or complete solubility in an oily phase, and at least one hydrophilic unit, in an amount sufficient to produce thickening of said oily phase, said hydrophilic unit being chosen from α,β-ethylenically unsaturated $C_3$–$C_6$ monocarboxylic acids, α,β-ethylenically unsaturated $C_4$–$C_6$ dicarboxylic acids and the monoester or monoamide derivatives of said diacids.

They are chosen from those disclosed and prepared in U.S. Pat. No. 5,736,125 (forming an integral part of the content of the application).

The hydrophobic unit or units of said thickening copolymers can be composed of $C_{10}$–$C_{22}$ alkyl (meth)acrylates; $C_{10}$–$C_{22}$ alkyl (meth)acrylamides; $C_{10}$–$C_{22}$ vinyl esters and ethers; siloxanes; $C_{10}$–$C_{22}$ α-olefins; fluorinated aliphatic side chains with at least 6 carbon atoms; or aliphatic side chains of ($C_1$–$C_{24}$)alkylstyrene with at least 6 carbon atoms and more particularly of $C_{18}$–$C_{22}$ alkyl (meth)acrylates. The hydrophobic unit or units generally represent from 80 to 98% by weight and preferably from 85 to 97% of the total weight of the thickening copolymer.

The hydrophilic unit or units of said thickening copolymers needed to thicken the oily phase can be composed of acrylic acid, methacrylic acid, maleic acid or itaconic acid or their monoesters or monoamides derived from $C_1$–$C_{22}$ alcohols and more particularly of acrylic acid and/or methacrylic acid.

The thickening copolymers in accordance with the invention generally have an acid number ranging from 0.1 to 4.0 meq/g and more particularly from 0.4 to 2 meq/g. Their average molecular weight is at least 50000 daltons and preferably varies from 50000 to 200000 daltons.

The thickening copolymers of the invention which are particularly preferred are chosen from $C_{10}$–$C_{22}$ alkyl (meth)acrylate/(meth)acrylic acid copolymers in which the amount of alkyl (meth)acrylate is sufficient to result in the partial or complete solubility of said polymer in an oily phase and the amount of (meth)acrylic acid is sufficient to thicken the oily phase.

They are more particularly still chosen from:

docosyl acrylate/styrene/acrylic acid copolymers in which the amount of docosyl acrylate and of styrene is sufficient to result in partial or complete solubility of said polymer in an oily phase and the amount of acrylic acid is sufficient to thicken the oily phase, such as the products disclosed under the names Sample 124–93 (72/4/2% by weight), Sample 124–130 (68/27/5% by weight) or Sample 108–195 (67/28/5% by weight) in U.S. Pat. No. 5,736,125 which are manufactured by Landec Corporation;

stearyl acrylate/methacrylic acid copolymers in which the amount of stearyl acrylate is sufficient to result in partial or complete solubility of said polymer in an oily phase and the amount of methacrylic acid is sufficient to thicken the oily phase, such as the products disclosed under the names Sample 124–194 (92.5/7.5% by weight) or Sample 124–195 (90/10% by weight) in U.S. Pat. No. 5,736,125 which are manufactured by Landec Corporation.

Generally, the thickening polymer or polymers of the invention can thus be present in the antisun compositions according to the invention or used in the process in accordance with the invention at contents which are generally between 0.1% and 10% by weight and preferably at contents of between 0.2% and 5% by weight with respect to the total weight of the composition.

The photostable antisun cosmetic compositions according to the invention can, of course, comprise, in addition to the dibenzoylmethane derivatives, one or more additional, hydrophilic or lipophilic, sunscreen agents which are active in the UV-A and/or UV-B regions. The presence of additional screening agents which are active in the UV-B region (wavelengths of between 280 nm and 320 nm approximately) thus makes it possible to have available final compositions capable of screening out all the UV rays.

The compositions of the invention can also comprise conventional cosmetic adjuvants chosen in particular from organic solvents, ionic or nonionic thickeners other than those in accordance with the invention, softeners, antioxidants, opacifiers, stabilizers, emollients, silicones, hydroxy acids, antifoaming agents, moisturizing agents, vitamins, fragrances, preservatives, surfactants, fillers, pigments (inorganic or organic), sequestering agents, polymers, propellants, basifying or acidifying agents, dyes or any other ingredient commonly used in cosmetics, in particular in the manufacture of antisun compositions in the form of emulsions. Of course, all the additional ingredients capable of being introduced into the compositions in accordance with the invention must be such that they do not disturb or detrimentally affect to a substantial extent the photostabilizing effect exerted by the thickening copolymers on the dibenzoylmethane derivatives.

The oily phase of the photoprotective compositions of the invention can be composed of at least one oil chosen from animal, vegetable, mineral or synthetic oils and in particular from liquid petrolatum, liquid paraffin, volatile or nonvolatile silicone oils, isoparaffins, poly-α-olefins, or fluorinated and perfluorinated oils known per se. It can also comprise waxes chosen from animal, fossil, vegetable, mineral or synthetic waxes known per se. It can also comprise fatty acids, fatty alcohols and fatty acid esters.

In order to obtain good photostability of the dibenzoylmethane derivative, the oily phase of the photoprotective compositions of the invention will not comprise isopropyl myristate and/or mineral oil when the thickening copolymer according to the invention used is the stearyl acrylate/methacrylic acid (92.5/7.5% by weight) copolymer.

Mention may be made, among organic solvents, of lower alcohols and polyols.

The additional thickeners can be chosen in particular from crosslinked polyacrylic acids or modified or unmodified guar gums and celluloses, such as hydroxypropylated guar gum, methylhydroxyethylcellulose, hydroxypropylmethylcellulose and hydroxyethylcellulose.

The compositions of the invention can be prepared according to techniques well known to a person skilled in the art, in particular those intended for the preparation of emulsions of oil-in-water or water-in-oil type.

These compositions can be provided in particular in the form of a simple or complex emulsion (O/W, W/O, O/W/O or W/O/W), such as a cream, a milk, a gel or a cream gel, of a powder or of a solid stick and can optionally be packaged as an aerosol and be provided in the form of a foam or of a spray.

When it is an emulsion, the aqueous phase of the latter can comprise a nonionic vesicular dispersion prepared according to known processes (Bangham, Standish and Watkins, J. Mol. Biol. 13, 238 (1965), FR 2 315 991 and FR 2 416 008).

The photostable cosmetic compositions of the invention can be used as compositions for protecting the human epidermis or the hair against ultraviolet rays, as antisun compositions or as make-up products.

When the cosmetic compositions according to the invention are used for the protection of the human epidermis against UV rays or as an antisun composition, they can be provided in the form of a gelled oil, of a suspension or dispersion in fatty substances, in the form of a nonionic vesicular dispersion or in the form of an emulsion, preferably of oil-in-water type, such as a cream or a milk, in the form of an ointment, gel, solid stick, aerosol foam or spray.

When the cosmetic compositions according to the invention are used for the protection of the hair, they can be provided in the form of a shampoo, lotion, gel, emulsion or nonionic vesicular dispersion and can constitute, for example, a rinse-out composition, to be applied before or after shampooing, before or after dyeing or bleaching and before, during or after perming or hair straightening, a styling or treating lotion or a styling or treating gel, a lotion or a gel for blow drying or hair setting, or a composition for perming or straightening, dyeing or bleaching the hair.

When the compositions are used as a product for making up the eyelashes, eyebrows or skin, such as a treatment cream for the epidermis, foundation, lipstick stick, eyeshadow, face powder, mascara or eyeliner, they can be provided in the anhydrous or aqueous, pasty or solid form, such as oil-in-water or water-in-oil emulsions, nonionic vesicular dispersions, or suspensions.

As indicated at the beginning of the description, a further subject matter of the present invention is a process for the cosmetic treatment of the skin or hair, intended to protect them against the effect of UV rays, which consists in applying, to the skin or hair, an effective amount of a photostable cosmetic composition as defined above.

Concrete, but in no way limiting, examples illustrating the invention will now be given.

EXAMPLE 1

In this example, the photostability of 4-(tert-butyl)-4'-methoxydibenzoylmethane (sunscreen agent "Parsol 1789" from Givaudan) were studied in the presence of a thickening copolymer according to the invention, namely: stearyl acrylate/methacrylic acid (92.5/7.5% by weight) copolymers disclosed under the name Sample 124–194 in U.S. Pat. No. 5,736,125.

By way of comparison, the photostability of this same screening agent was studied in the absence of this thickening polymer.

The photostability of 4-(tert-butyl)-4'-methoxydibenzoylmethane was also studied while varying the amount of thickening polymer.

The compositions of these three formulae (F0-F1-F2) were thus as follows (% by weight with respect to the total weight of the formula):

| | | |
|---|---|---|
| F0 (comparative) | Thickening polymer 0% | Common vehicle* |
| F1 (invention) | Thickening polymer 1.9% | Common vehicle* |
| F2 (invention) | Thickening polymer 3% | Common vehicle* |

*the composition of the common vehicle was itself as follows (% by weight with respect to the total weight of the formula):

| | |
|---|---|
| Thickening polymer Sample 124–194 from Landec Corp | X% |
| 4-tert-Butyl-4'-methoxydibenzoylmethane, sold under the name Parsol 1789 by Givaudan | 2% |
| $C_{12}/C_{15}$ Alkyl benzoates, sold under the name Finsolv TN by Finetex | 4% |
| Hexyldecanol/hexyldecyl laurate, sold under the name Cetiol PLG from Henkel | q.s for 100% |

The photostability of the sunscreen agent in these formulations was quantified by spectrophotometric quantitative determination of the residual screening agent after irradiating for two hours with a solar simulator. The exact procedure which was followed is as follows:

the formulae prepared are spread at a rate of 2 mg/cm² over a substrate made of depolished poly(methyl methacrylate);

the samples are subsequently subjected for two hours, at constant temperature, to the radiation of a Heraeus Suntest (Source: 1.8 kW xenon long arc), in order to simulate natural UV radiation (UV-A+UV-B);

after exposure, each sample is immersed in 55 ml of methanol in order to extract the sunscreen agent;

the compositions thus obtained are analyzed by UV spectrophotometry in the 290–400 nm range.

The level of residual screening agent after irradiation is expressed mathematically by the ratio of the concentration of screening agent measured in the irradiated sample to the initial concentration of this screening agent in the sample before irradiation.

The results obtained were as follows:

| Compositions | Residual Parsol 1789 after irradiating for 2 hours |
|---|---|
| F0 (comparative) | 4.07% (±3.75) |
| F1 (invention) | 35.74% (±5.55) |
| F2 (invention) | 43.20% (±4.65) |

These results clearly demonstrate the notable photostabilizing effect contributed by the thickening polymer in accordance with the invention with regard to 4-(tert-butyl)-4'-methoxydibenzoylmethane.

What is claimed is:

1. A process for the stabilization of at least one dibenzoylmethane derivative with respect to ultraviolet radiation in a vehicle comprising at least one oily phase, comprising combining said dibenzoylmethane derivative with an effective amount of at least one thickening copolymer comprising at least one hydrophobic unit, in an amount sufficient to result in its partial or complete solubility in said oily phase, and at least one hydrophilic unit, in an amount sufficient to produce thickening of said oily phase; said hydrophilic unit being selected from the group consisting of $\alpha,\beta$-ethylenically unsaturated $C_3$–$C_6$ monocarboxylic acids, $\alpha,\beta$-ethylenically unsaturated $C_4$–$C_6$ dicarboxylic acids, and the monoester or monoamide derivatives of said diacids, wherein said oily phase does not comprise isopropyl myristate and/or mineral oil when the thickening copolymer is a stearyl acrylate/methacrylic acid (92.5/7.5% by weight) copolymer.

2. The process as claimed in claim 1, wherein the hydrophobic unit or units of said thickening copolymer is comprised of $C_{10}$–$C_{22}$ alkyl (meth)acrylates; $C_{10}$–$C_{22}$ alkyl (meth)acrylamides; $C_{10}$–$C_{22}$ vinyl esters and ethers; siloxanes; $C_{10}$–$C_{22}$ $\alpha$-olefins; fluorinated aliphatic side chains with at least 6 carbon atoms; or aliphatic side chains of ($C_1$–$C_{24}$)alkylstyrene with at least 6 carbon atoms.

3. The process as claimed in claim 1, wherein the hydrophobic unit or units of said thickening copolymer is comprised of $C_{18}$–$C_{22}$ alkyl (meth)acrylates.

4. The process as claimed in claim 1, wherein the hydrophobic unit or units of said thickening copolymer represent from 80 to 98% of the total weight of the thickening copolymer.

5. The process as claimed in claim 1, where the hydrophilic unit or units of said thickening copolymer comprised acrylic acid or methacrylic acid, maleic acid or itaconic acid or their monoesters or monoamides derived from $C_1$–$C_{22}$ alcohols.

6. The process as claimed in claim 1, wherein the thickening copolymer exhibits an acid number ranging from 0.1 to 4.0 meq/g.

7. The process as claimed in claim 1, wherein the thickening copolymer exhibits at least 50000 daltons.

8. The process as claimed in claim 1, wherein the thickening copolymer comprises $C_{10}$–$C_{22}$ alkyl (meth)acrylate/(meth)acrylic acid copolymers in which the amount of alkyl (meth)acrylate is sufficient to result in a partial or complete solubility of said polymer in an oily phase and the amount of (meth)acrylic acid is sufficient to thicken the oily phase.

9. The process as claimed in claim 8, where the thickening copolymer comprises from docosyl acrylate/styrene/acrylic acid copolymers and/or stearyl acrylate/methacrylic acid copolymers in which the amount of docosyl acrylate and of styrene is sufficient to result in a partial or complete solubility of said polymer in an oily phase and the amount of acrylic acid is sufficient to thicken the oily phase.

10. The process as claimed in claim 9, where the thickening copolymer is selected from the group consisting of
docosyl acrylate/styrene/acrylic acid (7214/2% by weight) copolymer
docosyl acrylate/styrene/acrylic acid (68/27/5% by weight) copolymer
docosyl acrylate/styrene/acrylic acid (67/28/5% by weight) copolymer
stearyl acrylate/methacrylic acid (92.5/7.5% by weight) copolymer and
stearyl acrylate/methacrylic acid (90/10% by weight) copolymer.

11. The process as claimed in claim 1, wherein the dibenzoylmethane derivative or derivatives is selected from:
2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane;
2,6-dimethyl-4-tert-butyl-4'-methoxydibenzoylmethane;
or mixtures thereof.

12. The process as claimed in claim 11, where the dibenzoylmethane derivative is 4-(tert-butyl)-4'-methoxydibenzoylmethane.

13. The process as claimed in claim 11, where the dibenzoylmethane derivative is 4-isopropyldibenzoylmethane.

14. A photostable screening cosmetic composition for the photoprotection, by the topical route, of the skin and/or hair against ultraviolet radiation, comprising, in a cosmetically acceptable vehicle, at least one dibenzoylmethane derivative and at least one oily phase, which additionally comprises an effective amount of at least one thickening copolymer comprising at least one hydrophobic unit, in an amount sufficient to result in its partial or complete solubility in said oily phase, and at least one hydrophilic unit, in an amount sufficient to produce thickening of said oily phase; said hydrophilic unit selected from the group consisting of $\alpha,\beta$-ethylenically unsaturated $C_3$–$C_6$ monocarboxylic acids, $\alpha,\beta$-ethylenically unsaturated $C_4$–$C_6$ dicarboxylic acids, and the monoester or monoamide derivatives of said diacids; with the proviso that said oily phase does not comprise isopropyl myristate and/or mineral oil when the thickening copolymer is the stearyl acrylate/methacrylic acid (92.5/7.5% by weight) copolymer.

15. A composition as claimed in claim 14, wherein the hydrophobic unit or units of said thickening copolymer comprise of $C_{10}$–$C_{22}$ alkyl (meth)acrylates; $C_{10}$–$C_{22}$ alkyl (meth)acrylamides; $C_{10}$ –$C$22 vinyl esters and ethers; siloxanes; $C_{10}$–$C_{22}$ α-olefins; fluorinated aliphatic side chains with at least 6 carbon atoms; or aliphatic side chains of ($C_{1}$–$C_{24}$)alkylstyrene with at least 6 carbon atoms.

16. A composition as claimed in claim 14, wherein the hydrophobic unit or units of said thickening copolymer comprise of $C_{18}$–$C_{22}$ alkyl (meth)acrylates.

17. A composition as claimed in any one of claim 14, wherein the hydrophobic unit or units of said thickening copolymer represent from 80 to 98% total weight of the thickening copolymer.

18. A composition as claimed in claim 14, wherein the hydrophilic unit or units of said thickening copolymer comprise of acrylic acid or methacrylic acid, maleic acid or itaconic acid or their monoesters or monoamides formed from $C_{1}$–$C_{22}$ alcohols.

19. A composition as claimed in claim 14, wherein the thickening copolymer exhibits an acid number ranging from 0.1 to 4.0 meq/g.

20. A composition as claimed in claim 14, wherein the thickening copolymer exhibits at least 50000 daltons.

21. A composition as claimed in claim 14, wherein the thickening copolymer comprise $C_{10}$–$C_{22}$ alkyl (meth) acrylate/(meth)acrylic acid copolymers in which the amount of alkyl (meth)acrylate is sufficient to result in a partial or complete solubility of said polymer in an oily phase and the amount of (meth)acrylic acid is sufficient to thicken the oily phase.

22. A composition as claimed in claim 21, where the thickening copolymer comprise docosyl acrylate/styrene/ acrylic acid copolymers and stearyl acrylate/methacrylic acid copolymers in which the amount of docosyl acrylate and of styrene is sufficient to result in a partial or complete solubility of said polymer in an oily phase and the amount of acrylic acid is sufficient to thicken the oily phase.

23. A composition as claimed in claim 22, wherein the thickening copolymer is selected from the group consisting of:
   docosyl acrylate/styrene acrylic acid (72/4/2% by weight) copolymer
   docosyl acrylate/styrene acrylic acid (68/27/5% by weight) copolymer
   docosyl acrylate/styrene acrylic acid (67/28/5% by weight) copolymer
   stearyl acrylate/methacrylic acid (92.5/7.5% by weight) copolymer and
   stearyl acrylate/methacrylic acid (90/10% by weight) copolymer.

24. The process as claimed in claim 14, wherein the dibenzoylmethane derivative or derivatives is selected from:
   2-methyldibenzoylmethane;
   4-methyldibenzoylmethane;
   4-isopropyldibenzoylmethane;
   4-tert-butyldibenzoylmethane;
   2,4-dimethyldibenzoylmethane;
   2,5-dimethyldibenzoylmethane;
   4,4'-diisopropyldibenzoylmethane;
   4,4'-dimethoxydibenzoylmethane;
   4-tert-butyl-4'-methoxydibenzoylmethane;
   2-methyl-5-isopropyl-4'-methoxydibenzoylmethane;
   2-methyl-5-tert-butyl-4'-methoxydibenzoylmethane;
   2,4-dimethyl-4'-methoxydibenzoylmethane;
   2,6-dimethyl-4-tert-butyl-4'-methoxydibenzoylmethane;
   or mixtures thereof.

25. A composition as claimed in claim 24, where the dibenzoylmethane derivative is 4-(tert-butyl)-4,'-methoxydibenzoylmethane.

26. A composition as claimed in claim 24, where the dibenzoylmethane derivative is 4-isopropyldibenzoylmethane.

27. A composition as claimed in claim 14, wherein the content of dibenzoylmethane derivative(s) is between 0.01% and 10% by weight with respect to the total weight of the composition.

28. A composition as claimed in claim 27, wherein said content is between 0.1% and 6% by weight with respect to the total weight of the composition.

29. A composition as claimed in claim 14, wherein the content of thickening copolymer(s) varies from 0.1% to 10% by weight with respect to the total weight of the composition.

30. A composition as claimed in claim 29, wherein said content varies from 0.2% to 5% by weight with respect to the total weight of the composition.

31. A cosmetic treatment process for protecting the skin and/or hair against ultraviolet radiation, in comprising in applying, to the skin and/or hair, an effective amount of at least one composition as defined in any one of claims 14 to 29.

32. A method for stabilizing, with respect to UV radiation, a dibenzoylmethane derivative present in a cosmetic composition comprising at least one oily phase, said method comprising applying at least one thickening copolymer comprising at least one hydrophobic unit, in an amount sufficient to result in its partial or complete solubility in said oily phase, and at least one hydrophilic unit, in an amount sufficient to produce thickening of said oily phase; said hydrophilic unit being selected from the group consisting of α,β-ethylenically unsaturated $C_{3}$–$C_{6}$ monocarboxylic acids, α,β-ethylenically unsaturated $C_{4}$–$C_{6}$ dicarboxylic acids, and the monoester or monoamide derivatives of said diacids, wherein said oily phase does not comprise isopropyl myristate and/or mineral oil when the thickening copolymer is a stearyl acrylate/methacrylic acid (92.5/7.5% by weight) copolymer.

33. The process as claimed in claim 1, wherein the dibenzoylmethane derivative or derivatives is selected from:
   2-methyldibenzoylmethane;
   4-methyldibenzoyhmethane;
   4-isopropyldibenzoylmethane;
   4-tert-butyldibenzoylmethane;
   2,4-dimethyldibenzoylmethane;
   2,5-dimethyldibenzoylmethane;
   4,4'-diisopropyldibenzoylmethane;
   4,4'-dimethoxydibenzoylmethane;
   2-methyl-5-isopropyl-4'-methoxydibenzoylmethane;
   2-methyl-5-tert-butyl-4'-methoxydibenzoylmethane;
   2,4-dimethyl-4'-methoxydibenzoylmethane;
   2,6-dimethyl-4-tert-butyl-4'-methoxydibenzoylmethane;
   or mixtures thereof.

34. A composition as claimed in claim 14, wherein the dibenzoylmethane derivative or derivatives is selected from:

2-methyldibenzoylmethane;

4-methyldibenzoylmethane;

4-isopropyldibenzoylmethane;

4-tert-butyldibenzoylmethane;

2,4-dimethyldibenzoylmethane;

2,5-dimethyldibenzoylmethane;

4,4'-diisopropyldibenzoylmethane;

4,4'-dimethoxydibenzoylmethane;

2-methyl-5-isopropyl-4'-methoxydibenzoylmethane;

2-methyl-5-tert-butyl-4'-methoxydibenzoylmethane;

2,4-dimethyl-4'-methoxydibenzoylmethane;

2,6-dimethyl-4-tert-butyl-4'-methoxydibenzoylmethane;

or mixtures thereof.

* * * * *